(12) United States Patent
Yuan et al.

(10) Patent No.: US 12,239,682 B1
(45) Date of Patent: Mar. 4, 2025

(54) PEONY STAMEN-DODDER COMPOSITE, AND ITS PREPARATION METHOD AND APPLICATION

(71) Applicant: HEZE BRANCH, QILU UNIVERSITY OF TECHNOLOGY (SHANDONG ACADEMY OF SCIENCES), Heze (CN)

(72) Inventors: Wenpeng Yuan, Heze (CN); Dandan Cheng, Heze (CN); Zhiqiang Huang, Heze (CN)

(73) Assignee: HEZE BRANCH, QILU UNIVERSITY OF TECHNOLOGY (SHANDONG ACADEMY OF SCIENCES), Heze (CN)

( * ) Notice: Subject to any disclaimer, the term of this patent is extended or adjusted under 35 U.S.C. 154(b) by 0 days.

(21) Appl. No.: 18/948,016

(22) Filed: Nov. 14, 2024

Related U.S. Application Data

(63) Continuation of application No. PCT/CN2024/105571, filed on Jul. 15, 2024.

(30) Foreign Application Priority Data

Jul. 20, 2023 (CN) .......................... 202310896726.7

(51) Int. Cl.
*A61K 36/00* (2006.01)
*A61K 36/39* (2006.01)
*A61K 36/65* (2006.01)
*A61P 13/12* (2006.01)

(52) U.S. Cl.
CPC .............. *A61K 36/65* (2013.01); *A61K 36/39* (2013.01); *A61P 13/12* (2018.01); *A61K 2236/15* (2013.01); *A61K 2236/17* (2013.01); *A61K 2236/331* (2013.01); *A61K 2236/51* (2013.01); *A61K 2236/53* (2013.01)

(58) Field of Classification Search
CPC .................................................... A61K 36/65
See application file for complete search history.

(56) References Cited

U.S. PATENT DOCUMENTS

2004/0265397 A1  12/2004  Wang et al.

FOREIGN PATENT DOCUMENTS

| AU | 2002254842 A1 | 10/2003 |
|----|---------------|---------|
| CN | 102379969 A | 3/2012 |
| CN | 102599519 A | 7/2012 |
| CN | 105031135 A | 11/2015 |
| CN | 105819958 A * | 8/2016 |
| CN | 107875233 A | 4/2018 |
| CN | 113499369 A | 10/2021 |

OTHER PUBLICATIONS

Wenpeng Yuan et al., "Preparation of effervescent tablets with total nutrient extract from peony stamen", Cereals & Oils, Dec. 31, 2022, vol. 35, No. 1, pp. 106-110.
Zhijing Zheng et al., "Microcosmic clinical manual of western Chinese medicine", Published in Tianjin Science and Technology Translation and Publishing Co., LTD, Jan. 31, 2015, p. 363, penultimate paragraphs 1-2.
Yujuan Sun et al., "Value and cultivation techniques of Cuscuta chinensis Lam", Special Economic Animal and Plants, No. 6, Jun. 30, 2003, p. 25.
Wangxue,"Effectiveness of Peony Scented Tea", https://www.lvchashuo.com/baojiancha/22577.html, Nov. 24, 2021, Compare document 1, paragraphs 1, 5.
Xiaojuan Zhi Organized, "Shen Nong's Herb Classic", Guangdong Science & Technology Press, 2021, Dodder Part of p. 10.

* cited by examiner

*Primary Examiner* — Qiuwen Mi

(57) ABSTRACT

A peony stamen-dodder composite, which is prepared from 10-18 parts by weight of peony stamen and 5-12 parts by weight of dodder. In the preparation process, the peony stamen is sequentially subjected to desensitization, impregnation with a saline and drying, and the dodder is impregnated with a saline and baked. The pre-treated peony stamen and dodder are crushed, impregnated in warm water, ultrasonicated and filtered, and the filter residue is added with water, ultrasonicated and filtered. The filtrates are combined and concentrated under vacuum to obtain the desired composite. This application further provides an application of the composite in the treatment of nephritis.

5 Claims, 31 Drawing Sheets

PEONY STAMEN-DODDER COMPOSITE, AND ITS PREPARATION METHOD AND APPLICATION

CROSS-REFERENCE TO RELATED APPLICATIONS

This application is a continuation of International Patent Application No. PCT/CN2024/105571, filed on Jul. 15, 2024, which claims the benefit of priority from Chinese Patent Application No. 202310896726.7, filed on Jul. 20, 2023. The content of the aforementioned application, including any intervening amendments made thereto, is incorporated herein by reference in its entirety.

TECHNICAL FIELD

This application relates to traditional Chinese medicines, and more particularly to a peony stamen-dodder composite, and its preparation method and application.

BACKGROUND

The information disclosed in the background is intended only to promote the understanding of the disclosure, instead of necessarily acknowledging or in any way implying that the information constitutes the prior art known to those of ordinary skill in the art.

Chronic nephritis, mainly manifested as glomerulopathy, is characterized pathologically by damage of the glomerular basement membrane and inflammatory reactions. Common symptoms include proteinuria, hematuria, hypertension and edema. The pathogenesis diversity makes the course of chronic kidney diseases (CKD) usually long and slow. Prolonged glomerular injury and inflammatory response will lead to glomerulosclerosis and fibrosis, which may ultimately result in renal decompensation and development of chronic renal failure. Treatment strategies of CKD include controlling the etiological factors, controlling the development of underlying diseases such as hypertension and diabetes, controlling proteinuria and blood pressure, and application of nephroprotective agents. Therefore, for the patients suffering from CKD, the timely diagnosis and treatment are required to avoid further deterioration. Patients may usually remain asymptomatic for a long period of time, and obvious symptoms are observed until the kidney function is severely impaired. It should be particularly emphasized that chronic nephritis is not a single disease but refers to a group of diseases. CKDs can be classified into various types, and there is also an overlap between different types.

As an important part of peonies (*Paeonia suffruticosa* Andr.), stamen presents a conical or cylindrical shape, with a length of 2-4 cm and a diameter of 1-2 cm. The peony stamen mainly includes paeoniflorin, flavonoids, tannins, and volatile oils. Among these compounds, paeoniflorin is a compound with a wide range of biological activities including anti-inflammatory, antibacterial and anti-tumor activities. Flavonoids mostly have antioxidant, anti-inflammatory and anti-tumor effects. Tannins are astringent, hemostatic and antibacterial, and are often used to treat dysentery and diarrhea. Volatile oils have analgesic, sedative and antibacterial effects, and are commonly used in the treatment of headaches, neurasthenia, respiratory tract infections and other symptoms. Peony stamens are widely consumed as tea for its unique flavor and taste, but few studies have been carried out to evaluate its functional effects. The preliminary survey conducted on about 30 subjects demonstrates that for those subjects with regular consumption of the peony stamen tea, especially middle-aged and elderly women subjects, the frequent urination and high-frequency nocturia have been significantly improved.

At present, the treatment of CKD mainly relies on medication, nutritional support and dialysis. However, these treatment approaches have certain limitations, and cannot fully meet the needs of patients. Drug therapy mainly involves the use of thiazide diuretics, angiotensin converting enzyme inhibitors (ACEI)/angiotensin II receptor antagonists (ARB), glucocorticosteroids, cytotoxic drugs, and antiplatelet drugs to improve the symptoms of edema, hematuria, proteinuria, but these drugs have obvious side effects, and the treatment efficacy is not obvious or even ineffective for some patients with poor renal function. For those subjects with a creatinine (Cr) level greater than 264 mol/L, the drug administration should be performed carefully under close observation. The ACEI may raise side effects (e.g., persistent dry cough) in some patients, and in most cases, active application of glucocorticoids and cytotoxic drugs is recommended. The use of anti-infection drugs can only alleviate the external symptoms, and may also produce some side effects such as abdominal distension, cough, tonsillar redness and pain, and dry and sore throat. Botanical preparations that can improve nephritis symptoms and strengthen the kidney are ideal for the treatment of CKD, but there is a lack of botanical preparations that have significant therapeutic effects for CKD.

SUMMARY

An object of the disclosure is to provide a peony stamen-dodder composite, and its preparation method and application to overcome the defects in the prior art. Dodder (*Cuscuta chinensis* Lam.) is sweet and warm in nature, and is distributed in the kidney, liver and spleen meridians. Dodder is a medicine-food homologous resource with the effect of nourishing the liver and kidneys, securing essence and reducing urination, preventing miscarriage, improve eyesight, and checking diarrhea, which was first recorded in the "Shen Nong's Herb Classic" as the top-grade herb. The sweet herbs generally have a nourishing effect, and can tonify yang and replenish yin, with warm but not dry, and "tonifying without causing stagnation" characteristics. Sex hormones have the same effect of securing essence and preventing miscarriage. In the Chinese medicine, kidney is considered as the congenital foundation with the primordial yin and yang stored therein, and plays a significant role in promoting the reproductive development and functional activities of viscera and bowels. Peony stamen is the essence of *Paeonia suffruticosa* Andr., which is extremely rich in nutrition, containing a variety of mineral elements such as potassium, magnesium, calcium and phosphorus. Among which, the content of essential trace elements such as iron and zinc is several times higher than that of petals. In addition, stamens are naturally rich in squalene, Vitamin A, Vitamin C, Vitamin E and B vitamins, and contains 18 amino acids, where the primary amino acids are glutamic acid (3.63%) and aspartic acid (2.83%) in terms of content. The stamens are also rich in active polysaccharides, proteins, paeoniflorin, a-linolenic acid, catechins and other active components, making it an excellent raw material for natural health food. However, there are fewer studies on the functional evaluation of peony stamens, and application of peony stamens in the treatment of chronic kidney disease (CKD) has been rarely reported. It has only been reported on the preparation of a tea from stamens of the undeveloped *P.*

*ostii*. A preliminary investigation reveals that the regular consumption of peony stamens tea can significantly relieve the frequent urination and reduce the frequence of nocturia, especially for middle-aged and elderly subjects. Moreover, as proven by the preliminary animal experiment results, the peony stamen-containing composition has a better efficacy against the CKD rat model, which indicates that the peony stamen is an ideal natural plant source for the treatment of CKD, and has a brilliant development and application prospect. In the present disclosure, in order to explore a therapeutic effect of peony stamens on CKD, the peony stamen is compounded with the dodder, in conjunction with diluted saline impregnation, to guide the drug to the kidney meridian. The pharmacological experimental evaluation and human test demonstrate that the peony stamen-dodder composite has a better therapeutic effect on CKD, and its preparation method has also been determined. The therapeutic effect of the composite on CKD is verified by a CKD rat model. The administration of the decoction of the peony stamen-dodder composite can significantly improve the symptoms of nephritis in human, such as frequent urination, which provides a new therapy for CKD.

Technical solutions of the present disclosure are described as follows.

In a first aspect, this application provides a peony stamen-dodder composite, wherein raw materials of the peony stamen-dodder composite comprises 10-18 parts by weight of a peony stamen and 5-12 parts by weight of a dodder.

In some embodiments, the raw materials of the peony stamen-dodder composite comprise 15 parts by weight of the peony stamen and 8 parts by weight of the dodder.

In some embodiments, the peony stamen is a stamen of *Paeonia ostia*, a stamen of *Paeonia rockii*, or a combination thereof.

In a second aspect, this application provides a preparation method of the peony stamen-dodder composite described in the first aspect, comprising:

step (1) subjecting the peony stamen to desensitization, impregnation with a first saline for 10 min and drying, and subjecting the dodder to impregnation with a second saline for 20 min and baking; and step (2) crushing a treated peony stamen obtained in step (1), and crushing a treated dodder obtained in step (1); impregnating a crushed peony stamen and a crushed dodder with warm water followed by a first ultrasonic treatment and filtration to obtain a first filtrate and a filter residue; dispersing the filter residue in water followed by a second ultrasonic treatment and filtration to obtain a second filtrate; and combining the first filtrate with the second filtrate followed by vacuum concentration to obtain the peony stamen-dodder composite.

In some embodiments, in step (1), the desensitization is performed at 120° C. for 1-3 min, or performed by microwave-assisted desensitization at a power of 3,000-5,000 W and a temperature of 65-80° C. for 1-3 min; a thickness of the peony stamen is 3-6 mm.

In some embodiments, in step (1), the drying is performed at 55-65° C. for 4.5-5.5 h, and the baking is performed at 75-85° C. for 7.5-8.5 h.

In some embodiments, in step (1), the first saline and the second saline are light saline with a concentration of 1.2-1.8%, a weight of the first saline is 1-2 times a weight of the peony stamen, a weight of the second saline is 0.25-2 times the weight of the peony stamen, and the impregnation of the peony stamen is performed for 8-15 min, and the impregnation of the dodder is performed for 15-25 min.

In some embodiments, in step (2), a weight of the warm water is 19-21 times a total weight of the peony stamen and the dodder, a temperature of the warm water is 65-75° C., and the crushed peony stamen and the crushed dodder are impregnated in the warm water for 1.5-2.5 h.

In some embodiments, in step (2), the first ultrasonic treatment is carried out for 25-35 min, and the second ultrasonic treatment is carried out for 55-65 min; a weight of the water for dispersing the filter residue is 14-16 times a total weight of the peony stamen and the dodder.

In some embodiments, in step (2), a temperature of the vacuum concentration does not exceed 70° C., and the vacuum concentration is performed such that a weight of a concentrated product is 7.9-8.1 times the total weight of the peony stamen and the dodder.

In a third aspect, this application provides a method for treating nephritis and/or a food and/or health product in a subject in need thereof, comprising:

administering a therapeutically effective amount of the peony stamen-dodder composite described in the first aspect to the subject.

In a fourth aspect, this application provides a drug for treating nephritis, wherein the drug comprises the peony stamen-dodder composite described in the first aspect and a pharmaceutically acceptable adjuvant.

Compared to the prior art, the present disclosure has the following beneficial effects.

The therapeutic effect of the peony stamen-dodder composite provided herein has been demonstrated by treating rat models of CN with different doses of the composite in the form of freeze-dried powder. After one week of the treatment, urinary albumin excretion decreases significantly (P<0.05) in the positive control group and the high-dose group when compared to the model group. After two weeks of the treatment, the urinary albumin excretion in the positive control group and the high-dose group decreases significantly (P<0.05) when compared with the model group. Compared with the model group, uric acid, blood urea nitrogen (BUN) and creatinine (Cr) levels are significantly lower in the positive control group and the high, medium and low dose groups (P<0.01, P<0.05). In particular, the levels of uric acid, BUN, and Cr in the high-dose group (P<0.01) are close to those of the positive control group. The kidney weight and kidney/body weight ratio are significantly reduced in all dose groups, and in particular, the high-dose group exhibits a significant decline in the right kidney weight, and the reduction of the right kidney weight is associated with the dose (that is, a more obvious decline will be observed when the administration dose exceeds the high-dose group). Moreover, the pathological changes in the rat kidney are significantly relieved in the low, medium and high dose groups. As can be seen from the expression results of deposition of glomerular immunofluorescences C3 and IgG, the expression level of glomerular C3 and IgG deposition can be significantly reduced in the high-dose group (P<0.01). As can be seen from the expression results of IL-β in kidney, the positive control group and the high-dose group both exhibit a significantly reduced IL-13 expression level in the kidney, and there is no significant difference between the medium-dose and low-dose groups and the model group. Moreover, in the positive control group and all dose groups, the TNF-α expression is downregulated in the kidney. Combined with results of 24-h urinary protein level, uric acid, BUN, Cr level, pathological morphology examination and protein expression, it can be concluded that the composite of the present disclosure has a significant therapeutic effect on the rat CN model.

The peony stamen-dodder composite provided herein has significant therapeutic effects on the rat model of CN in a dose-dependent manner.

The peony stamen-dodder composite provided herein has simple preparation, and can be further processed into medicine, food or health care products, exhibiting a brilliant application prospect.

BRIEF DESCRIPTION OF THE DRAWINGS

The accompanying drawings are provided to facilitate the understanding of the technical solutions of the present disclosure, and form a part of the specification to illustrate the disclosure together with the embodiments. The accompanying drawings are illustrative and exemplary, and are not intended to limit the disclosure.

FIG. 1B: model group, at a magnification of 400×; FIG. 1C: positive control group, at a magnification of 400×; FIG. 1D: high-dose group, at a magnification of 400×; FIG. 1E: medium-dose group, at a magnification of 400×; and FIG. 1F: low-dose group, at a magnification of 400×);

FIG. 2B: model group; FIG. 2C: positive control group; FIG. 2D: high-dose group; FIG. 2E: medium-dose group; and FIG. 2F: low-dose group);

FIG. 3B: model group; FIG. 3C: positive control group; FIG. 3D: high-dose group; FIG. 3E: medium-dose group; and FIG. 3F: low-dose group);

DETAILED DESCRIPTION OF EMBODIMENTS

Figure 1A:
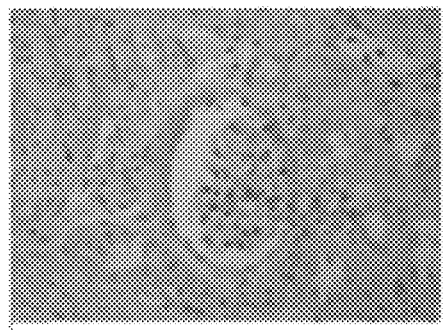
FIGS. 1A-1F show pathological sections of rat models of chronic nephritis (CN) from different groups in accordance with Example 2 of the present disclosure (FIG. 1A: blank control group, at a magnification of 400×.

In order to enable those skilled in the art to understand the technical solution of the present disclosure more clearly, the technical solutions of the present disclosure will be described in detail below in combination with specific embodiments.

Example 1

*Paeonia ostii* or *P. rockii* stamens were harvested from the end of March to the middle of April, with the pollen exposed at the stamen top, all the sepals splitting, and the stamens being visible with the naked eye, and the stamen collection should be finished by 10:00 a.m. every day. When the temperature was low, the collection time could be delayed appropriately. Fresh stamens were desensitized, treated with light saline and dried at 60° C. for 5 h, so that a variety of nutrients within the stamens, including amino acids, proteins, polysaccharides, flavonoids, vitamin E, and vitamin B3, were slowly accumulated into a dry substance. Dodder (*Cuscuta chinensis* Lam.) was treated with light saline and baked at 80° C. for 8 h.

15 parts by weight of pre-treated peony stamens and 8 parts by weight of the pre-treated dodder were crushed, impregnated with water at 70° C. for 2 h (a ratio of a weight of the water to a total weight of the pre-treated peony stamens and the pre-treated dodder is 20:1), ultrasonicated for 30 min and filtered to collect a first filtrate and a filter residue. The filter residue was added with water (a ratio of a weight of the water to a total weight of the pre-treated peony stamens and the pre-treated dodder is 15:1), ultrasonicated for 1 h and filtered to collect a second filtrate. The first filtrate and the second filtrate were combined and concentrated under vacuum at a temperature not higher than 70° C. to 8 times the weight of the total weight of the peony stamens and dodder, and freeze-dried to obtain a freeze-dried powder of the peony stamen-dodder composite.

Example 2

48 SD male rats, weighing (220±10) g and aged (6±1) weeks, were taken, and raised at a temperature of (22±2°) C and a humidity of 55%+5% with 12 h of light and 12 h of darkness alternately.

The rat model of chronic nephritis (CN) was improved according to Border's method. Firstly, an appropriate amount of Cationic Bovine Serum Albumin (cBSA) dried powder was dissolved in phosphate buffer solution (PBS) (pH 7.2-7.4) and mixed with incomplete Freund's adjuvant in a volume ratio of 1:1 to form a milky white suspension with a concentration of 2 mg/mL. Next, the rats were fasted for 12 h with free water access, and injected with 2 mL of a 2 mg/mL C-BSA solution on the back, axillae, and groin, once on days 1 and 8, respectively. From day 10, the rats were injected with C-BSA (16 mg·kg$^{-1}$) via the tail vein three times a week. After consecutive 3-week immunization, the rats were observed and analyzed. At the third week after the completion of the injection, the urine of rats was collected for 24 hours. The test results showed that compared with the blank control group, the C-BSA injection groups exhibited an obvious proteinuria symptom, suggesting that the rat model of CN was successfully established under the induction of C-BSA.

The successfully-established rat models of CN were randomly grouped into a model control group, a positive control group, a high-dose group (20 mg/(kg·d) freeze-dried powder of the peony stamen-dodder composite of Example 1), a medium-dose group (10 mg/(kg·d) freeze-dried powder of the peony stamen-dodder composite of Example 1), and a low-dose group (5 mg/(kg·d) freeze-dried powder of the peony stamen-dodder composite of Example 1), and a blank control group was set with normal rats, 8 rats in each group. The dosage was calculated using the body surface area calculation method. The positive control group was treated with ShenYan SiWei capsule (Wuhan Shuanglong Pharmaceutical Co., Ltd) at a dose of 3 g/(kg·d); the model group and the blank control group were treated with the equal amount of normal saline by irrigation, once a day for 4 weeks.

The urinary protein level was determined after the CN model was established, and at week 1, week 2 and week 4 of the administration. Before each determination, the rats were placed in metabolic cages for 24 h, and the urine was collected to detect the urine volume, and then analyzed with a semi-automatic biochemical analyzer for the urinary protein level.

After the 4$^{th}$ week of administration treatment, 1-3 ml of blood was taken from the inner canthus of the eyes of the rats for processing and the levels of uric acid, blood urea nitrogen (BUN) and creatinine (Cr) of the rats were measured using kits.

After the last blood sampling, the rats were sacrificed by cervical dislocation, and the right and left kidneys were isolated and weighed. The ratio of the total weight of the right and left kidneys to body weight (kidney/body ratio) was calculated.

The pathological examination of renal tissues was performed as follows. The renal tissues were washed with PBS to remove the surface envelope, placed in a 10% formalin solution for fixation, dehydrated stepwise with ethanol, embedded with paraffin and cut into 3-4 km-thick sections, which were stained with Hematoxylin and Eosin (HE) and observed under the microscope for pathological changes.

The pathological examination of glomeruli and renal tubules was performed as follows. The glomeruli and renal tubules were washed with normal saline, immersed in a 10% neutral formaldehyde solution for fixation, dehydrated, embedded with paraffin and cut into 3-μm-thick sections, which were subjected to periodic acid-Schiff (PAS) staining to observe pathological changes in the glomeruli. In addition, under the HE staining condition, 10 fields with only renal tubules but no glomeruli were randomly selected to perform semi-quantitative determination for tubulointerstitial damage and renal inflammatory cell infiltration.

Rat kidney tissues were taken and embedded with optimal cutting temperature compound (OTC), cut into 4 μm sections using a freezing microtome (cryostat), fixed in pre-cooled acetone for 10 min, washed to obtain a prepared section. The prepared section is incubated by dropping with FITC-labelled IgG antibody (1:50) for 30 min at 37° C. avoiding light, after washing the antibody, 50% glycerol were added dropwise to seal the section, and glomerular IgG deposition was observed under a fluorescence microscope. The section was taken and incubated with 5% BSA at room temperature for 30 min; after washing, C3 antibody (1:100) was added dropwise and incubated overnight at 4° C.; after washing the antibody, FITC-labelled secondary antibody was added dropwise and incubated in a wet box at 37° C. for 1 h away from light; after washing the antibody, 50% glycerol was added dropwise to seal the section, and the glomerular C3 deposition was observed under the fluorescence microscope.

The protein expression results of tumor necrosis factor-a (TNF-α) and interleukin-1β (IL-β) in rat left kidney tissues were observed by immunohistochemical staining.

The results were analyzed by using SPSS software, which were expressed as (x±s), and the comparison between groups was conducted by T-test ($P<0.05$ indicated the difference was statistically significant).

As shown in Table 1, after 1 week of treatment, the urinary protein excretion in the positive control group and the high-dose group decreased significantly ($P<0.05$) compared with the model group. After 2 weeks of treatment, the urinary protein excretion decreased significantly in the positive control group and the high-dose group compared to the model group ($P<0.05$). The low and medium dose groups were also able to reduce the urinary protein level in the rat model of CN after 1 week, 2 weeks and 4 weeks of treatment, but did not reach statistical significance ($P>0.05$). In conclusion, low, medium and high dose groups of freeze-dried powder of the peony stamen-dodder composite were able to reduce the urinary protein level in the treatment of the rat model group of CN. But there was a certain quantative-effective relationship, with insufficient dosage, the effect was unsatisfactory, and the therapeutic effect was significant when compared with the positive control group in the case of an appropriate dosage.

TABLE 1

Changes in urinary protein level in different groups of CN rat models (n = 8)

| Group | Post-modelling | 1 week of treatment | 2 weeks of treatment | 4 weeks of treatment |
|---|---|---|---|---|
| Blank control group | 11.92 ± 1.02 | 11.41 ± 1.70 | 11.04 ± 0.71 | 11.55 ± 0.92 |

TABLE 1-continued

Changes in urinary protein level in different groups of CN rat models (n = 8)

| Group | Post-modelling | 1 week of treatment | 2 weeks of treatment | 4 weeks of treatment |
|---|---|---|---|---|
| Model group | 48.92 ± 0.34** | 45.10 ± 1.12** | 41.95 ± 2.37** | 40.54 ± 1.68** |
| Positive control group | 48.32 ± 1.66** | 29.00 ± 1.85*# | 27.06 ± 1.54*# | 16.47 ± 1.76*## |
| Low-dose group | 48.06 ± 0.86** | 43.32 ± 2.43** | 40.21 ± 1.36** | 35.98 ± 3.49** |
| Medium-dose group | 48.75 ± 0.76** | 43.90 ± 0.62** | 40.85 ± 0.68** | 38.16 ± 1.28** |
| High-dose group | 48.56 ± 1.55** | 42.58 ± 3.53**# | 35.32 ± 3.29**# | 34.28 ± 2.55**# |

**compared with blank control group, P < 0.01;
*compared with blank group, P < 0.05;
compared with model group, P < 0.01;
compared with model group, P < 0.05.

BUN, Cr, and uric acid levels can reflect the glomerular filtration function, which can reflect the patient's renal function through the detection of their levels. As shown in Table 2, uric acid, BUN, and Cr were significantly higher in the model group after the fourth week of CN rat model administration treatment compared to the blank control group (P<0.01). Compared with the model group, uric acid, BUN, and Cr levels were significantly lower in the positive control group and the high, medium, and low dose groups (P<0.01, P<0.05). In particular, the levels of uric acid, BUN, and Cr in the high-dose group (P<0.01) were close to those of the positive control group.

TABLE 2

Uric acid, BUN and Cr levels in different groups of rat models of CN (n = 8)

| Group | Uric acid (μmol/L) | BUN (mmol/L) | Cr (μmol/L) |
|---|---|---|---|
| Blank control group | 284.54 ± 22.97 | 12.79 ± 0.94 | 181.82 ± 8.58 |
| Model group | 677.72 ± 27.54** | 31.62 ± 1.61** | 436.26 ± 12.17** |
| Positive control group | 380.97 ± 17.04*## | 14.44 ± 0.38**## | 216.56 ± 16.26*## |
| High-dose group | 442.85 ± 23.58*## | 17.31 ± 0.59**## | 289.10 ± 9.04**## |
| Medium-dose group | 453.71 ± 17.55**# | 20.64 ± 1.44**## | 324.11 ± 23.19**## |

TABLE 2-continued

Uric acid, BUN and Cr levels in different groups of rat models of CN (n = 8)

| Group | Uric acid (μmol/L) | BUN (mmol/L) | Cr (μmol/L) |
|---|---|---|---|
| Low-dose group | 538.88 ± 30.25**# | 23.87 ± 1.02**# | 368.43 ± 2.93**# |

**compared with blank control group, P < 0.01;
*compared with blank group, P < 0.05;
compared with model group, P < 0.01;
compared with model group, P < 0.05.

As shown in Table 3, the model group in the rat model of CN had significantly higher (P<0.05 or P<0.01) in terms of left kidney weight, right kidney weight, kidney/body ratio (left), kidney/body ratio (right) and kidney body/ratio (total) after the last blood sampling compared with the blank control group. It indicated that renal swelling in CN rats could not be self-healed without treatment.

The positive control group as well as the low, medium and high dose groups showed a decreasing trend in left kidney weight, right kidney weight, kidney/body ratio (left), kidney/body ratio (right), and kidney/body ratio (total) as compared to the model group. In particular, in the high-dose group, the kidney/body ratio (total) and kidney/body ratio (right) of the rat model of CN were significantly decreased (P<0.05), whereas in the medium-dose group, the weight of the right kidney of the rat model of CN was decreased, but it did not reach the statistical significance (P>0.05).

These results suggested that the dose of freeze-dried composite powder alleviated the symptoms of renal swelling in a rat model of CN. Specifically, the high-dose group exhibited a significant decline in the right kidney weight, and the reduction of the right kidney weight was associated with the dose (that was, a more obvious decline would be observed when the administration dose exceeded the high-dose group).

TABLE 3

Kidney/body ratios in different groups of rat models of CN (n = 6)

| Group | Weight (g) | Left kidney (g) | Right kidney (g) | kidney/body ratio (left) | kidney/body ratio (right) | kidney/body ratio (total) |
|---|---|---|---|---|---|---|
| Blank control group | 415.75 ± 13.33 | 1.22 ± 0.09 | 1.25 ± 0.07 | 0.29 ± 0.02 | 0.30 ± 0.01 | 0.59 ± 0.03 |
| Model group | 411.00 ± 8.00 | 1.72 ± 0.04** | 1.77 ± 0.02** | 0.42 ± 0.02* | 0.43 ± 0.01* | 0.85 ± 0.02** |
| Positive control group | 448.00 ± 8.83* | 1.46 ± 0.06*# | 1.46 ± 0.06*# | 0.33 ± 0.01*# | 0.33 ± 0.01# | 0.65 ± 0.01*# |

TABLE 3-continued

Kidney/body ratios in different groups of rat models of CN (n = 6)

| Group | Weight (g) | Left kidney (g) | Right kidney (g) | kidney/body ratio (left) | kidney/body ratio (right) | kidney/body ratio (total) |
|---|---|---|---|---|---|---|
| High-dose group | 421.33 ± 6.65 | 1.56 ± 0.08* | 1.58 ± 0.06* | 0.36 ± 0.02* | 0.36 ± 0.02*# | 0.72 ± 0.04**# |
| Medium-dose group | 407.50 ± 28.11 | 1.56 ± 0.22* | 1.53 ± 0.21 | 0.38 ± 0.03* | 0.38 ± 0.03* | 0.76 ± 0.05** |
| Low-dose group | 441.25 ± 37.06 | 1.58 ± 0.16* | 1.60 ± 0.19* | 0.37 ± 0.02* | 0.37 ± 0.03* | 0.75 ± 0.05** |

**compared with blank control group, $P < 0.01$;
*compared with blank group, $P < 0.05$;
compared with model group, $P < 0.01$;
compared with model group, $P < 0.05$.

Figure 1B:
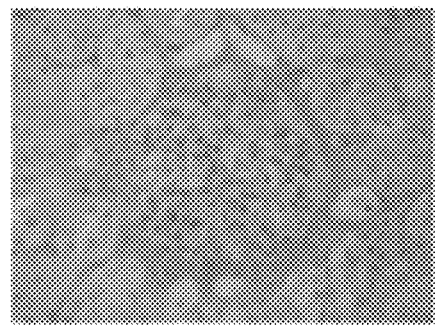
Figure 1C:
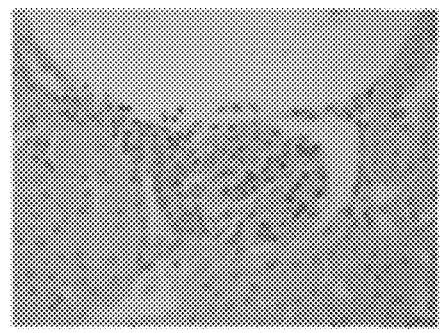
Figure 1D:
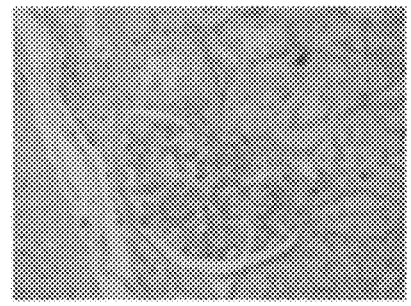
Figure 1E:
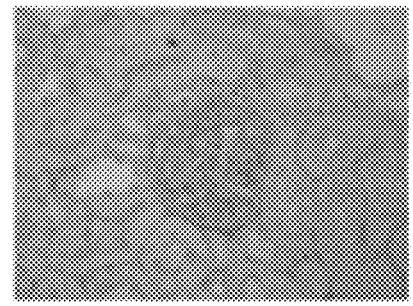
Figure 1F:
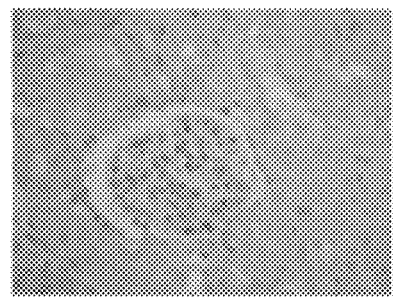

As shown in FIG. 1A-1F, compared with the blank control group, the basement membrane in the kidney tissue of CN rats in the model group showed a distinct purplish red color with uneven thickness. The thickness of glomerular basement membrane was uniformly distributed in the kidney tissues of rats in the positive control group and in the different dose group, especially in the high-dose group, as compared to the model group. This suggests that the peony stamen-dodder composite herein can improve the pathological morphology of kidneys in a rat model of CN.

Figure 2A:
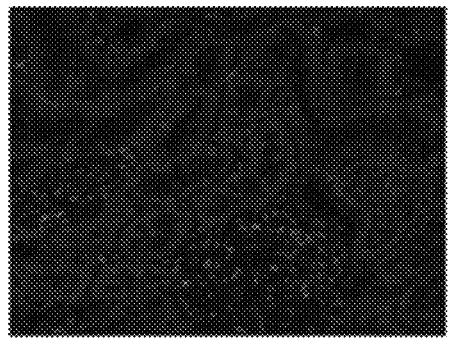
FIGS. 2A-2F schematically show expression of glomerular immunofluorescence C3 deposition in CN rat models from different groups in accordance with Example 2 of the present disclosure (FIG. 2A: blank control group.
Figure 2B:
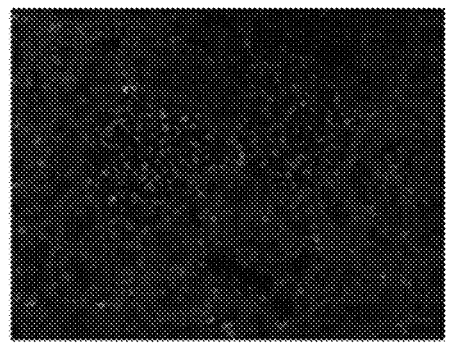
Figure 2C:
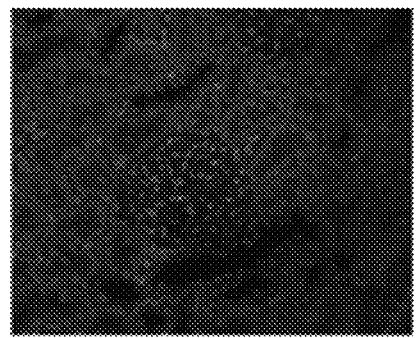
Figure 2D:
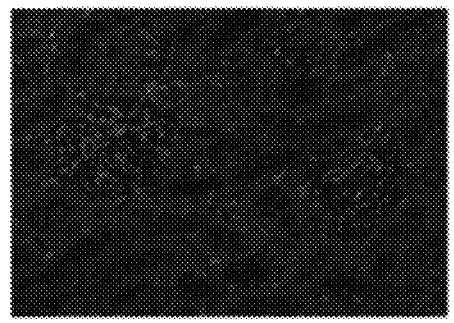
Figure 2E:
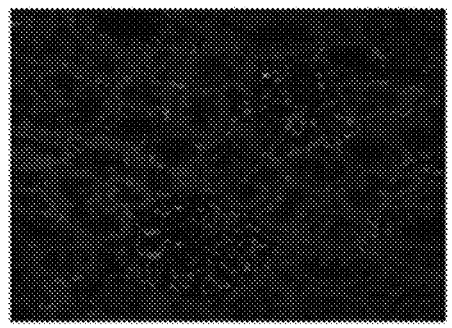
Figure 2F:
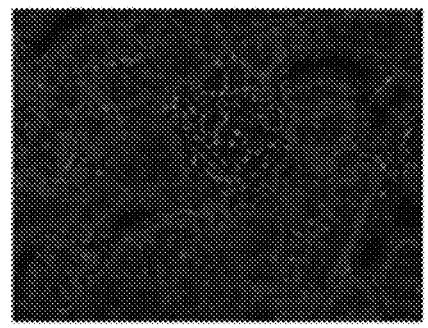

As can be seen from the expression results of glomerular immunofluorescence C3 deposition that the blank group was expressed at a micro level, while the model group showed an elevated expression in FIG. 2A-2F. The positive control group and the high-dose group were able to reduce the expression level of glomerular C3 deposition, which was lower in the medium-dose group than in the low-dose group.

Figure 3A:
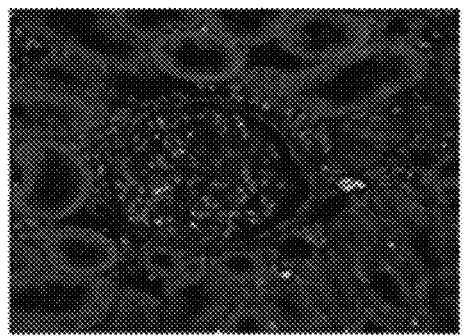
FIGS. 3A-3F schematically show expression of glomerular immunofluorescence IgG deposition in CN rat models from different groups in accordance with Example 2 of the present disclosure (FIG. 3A: blank control group.
Figure 3B:
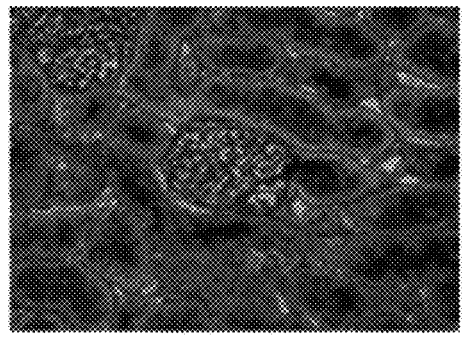
Figure 3C:
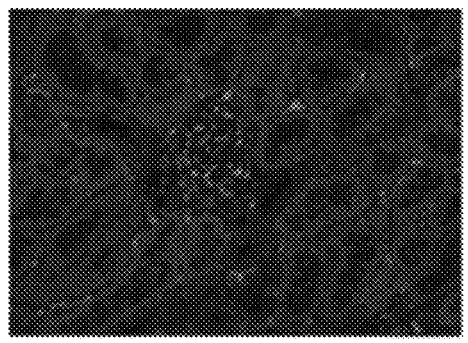
Figure 3D:
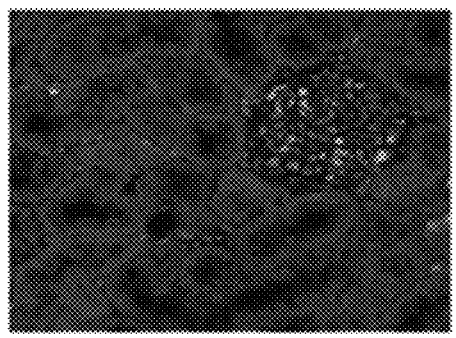
Figure 3E:
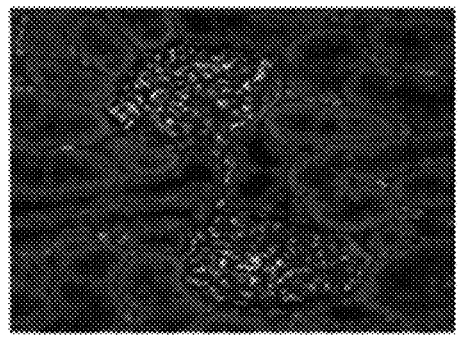
Figure 3F:
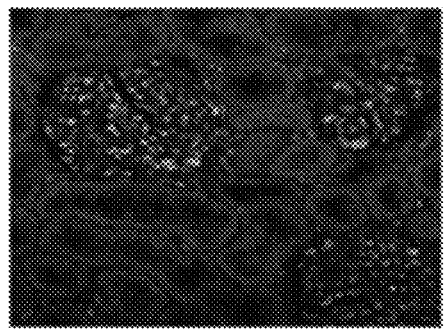

As can be seen from the expression results of deposition of glomerular immunofluorescence IgG in FIGS. 3A-3F, the blank group of deposition of glomerular immunofluorescence IgG was expressed at a micro level while the model group of which was expressed at a high level. The expression of the positive control group of deposition of glomerular C3 was close to that of the blank group, whereas the high-dose group was at a low expression level, and the expression level in the medium-dose group was essentially close to that in the low-dose group. Combined with results of 24-h urinary protein level, uric acid, BUN, Cr level, pathological morphology examination and protein expression, it can be concluded that the composite of the present disclosure has a significant therapeutic effect on the rat CN model.

Figure 4:
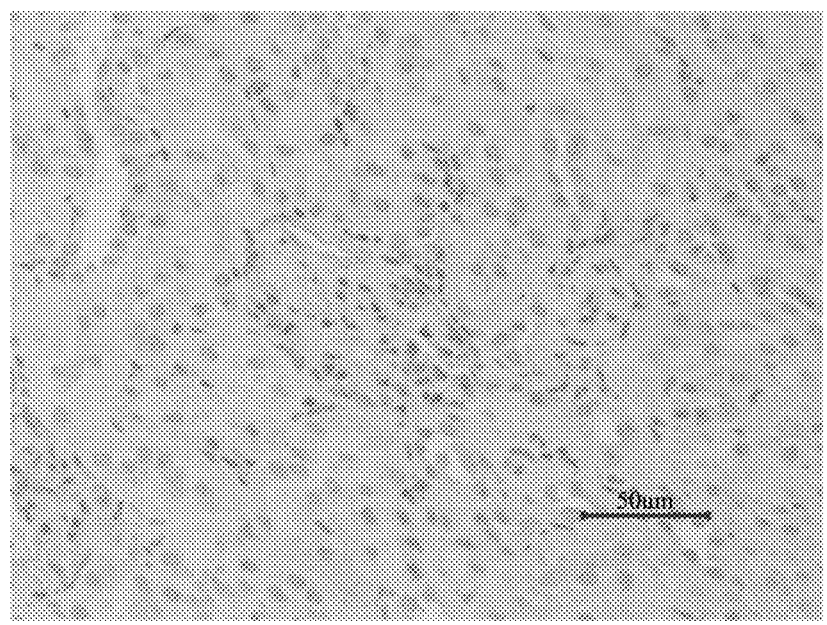
FIG. 4 is an immunohistochemical image of the No. 3 CN rat model in a blank control group in accordance with Example 2 of the present disclosure (at a magnification of 400×)
Figure 5:
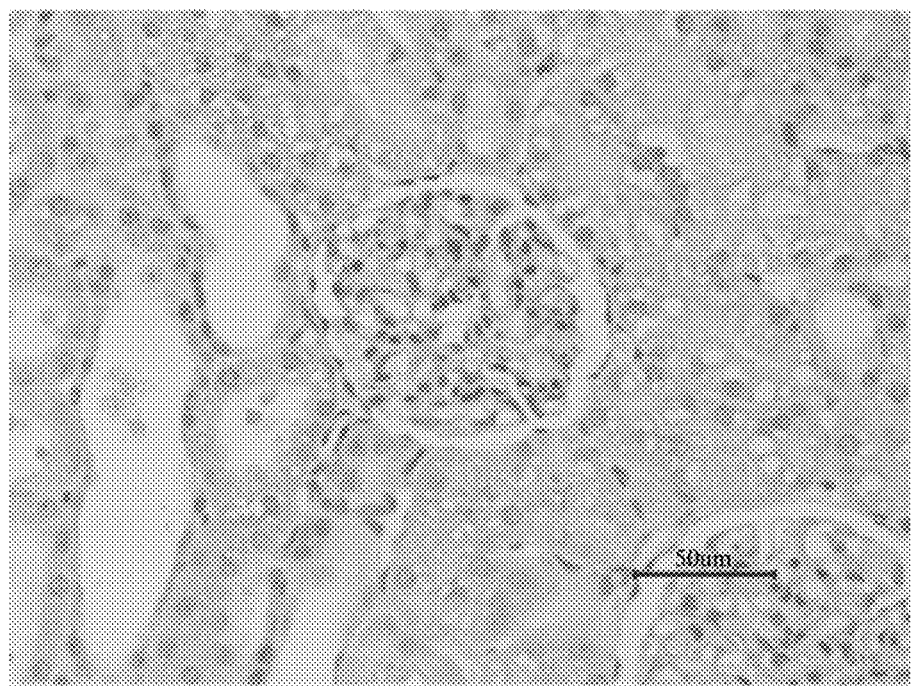
FIG. 5 is an immunohistochemical image of the No. 9 CN rat model in a model group in accordance with Example 2 of the present disclosure (at a magnification of 400×)
Figure 6:
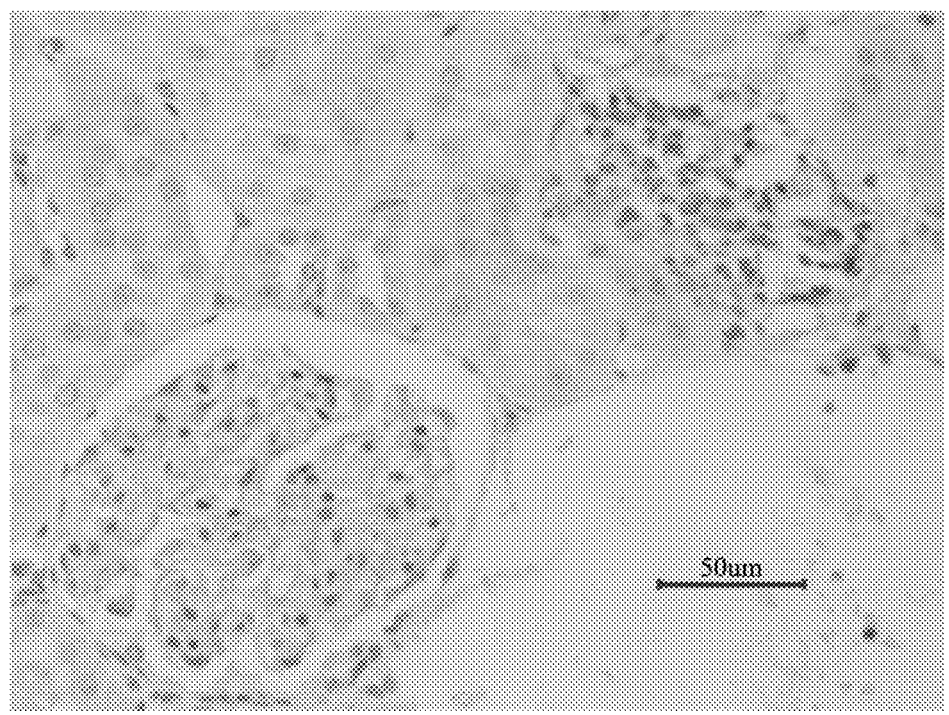
FIG. 6 is an immunohistochemical image of the No. 12 CN rat model in a model group in accordance with Example 2 of the present disclosure (at a magnification of 400×)
Figure 7:
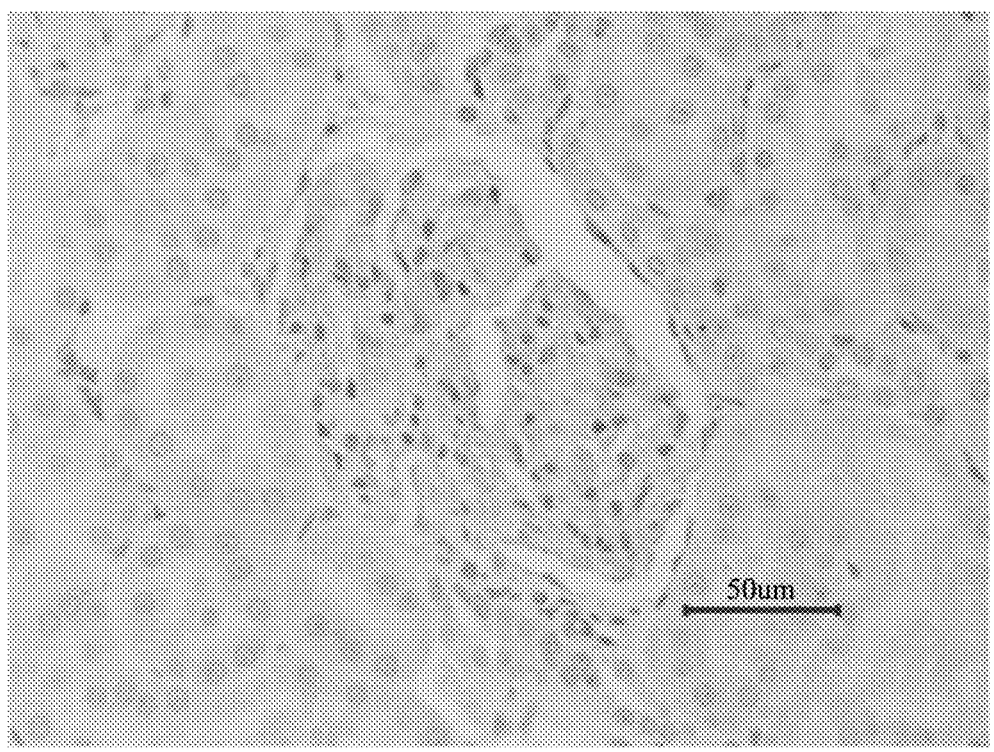
FIG. 7 is an immunohistochemical image of the No. 15 CN rat model in a positive control group in accordance with Example 2 of the present disclosure (at a magnification of 400×)
Figure 8:
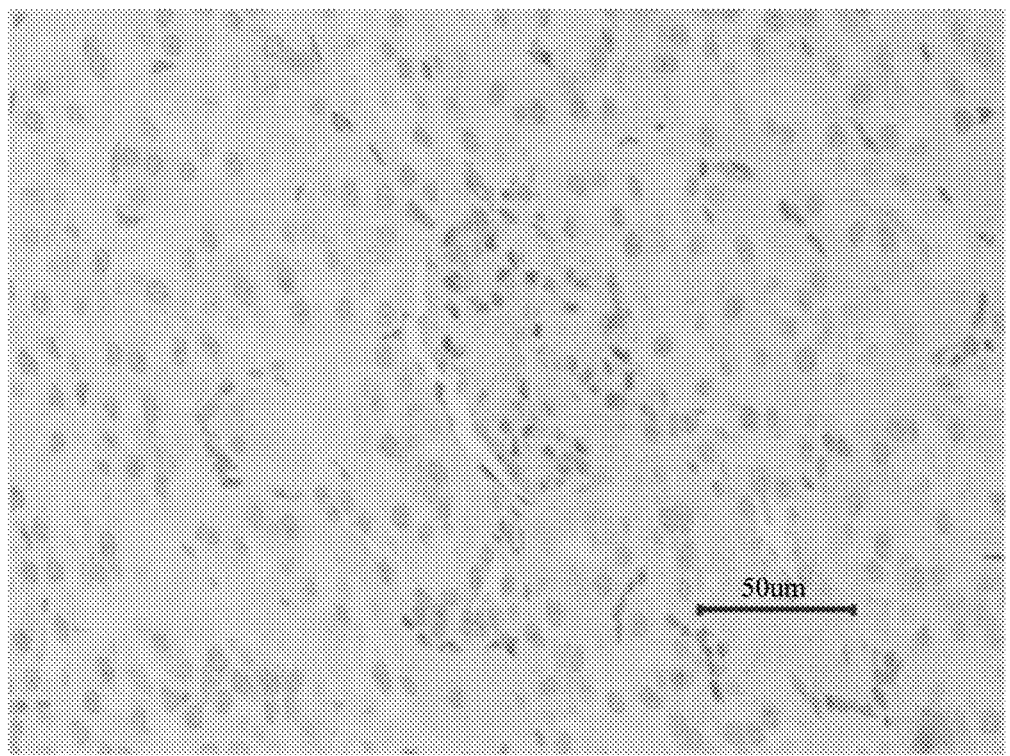
FIG. 8 is an immunohistochemical image of the No. 18 CN rat model in a positive control group in accordance with Example 2 of the present disclosure (at a magnification of 400×)
Figure 9:
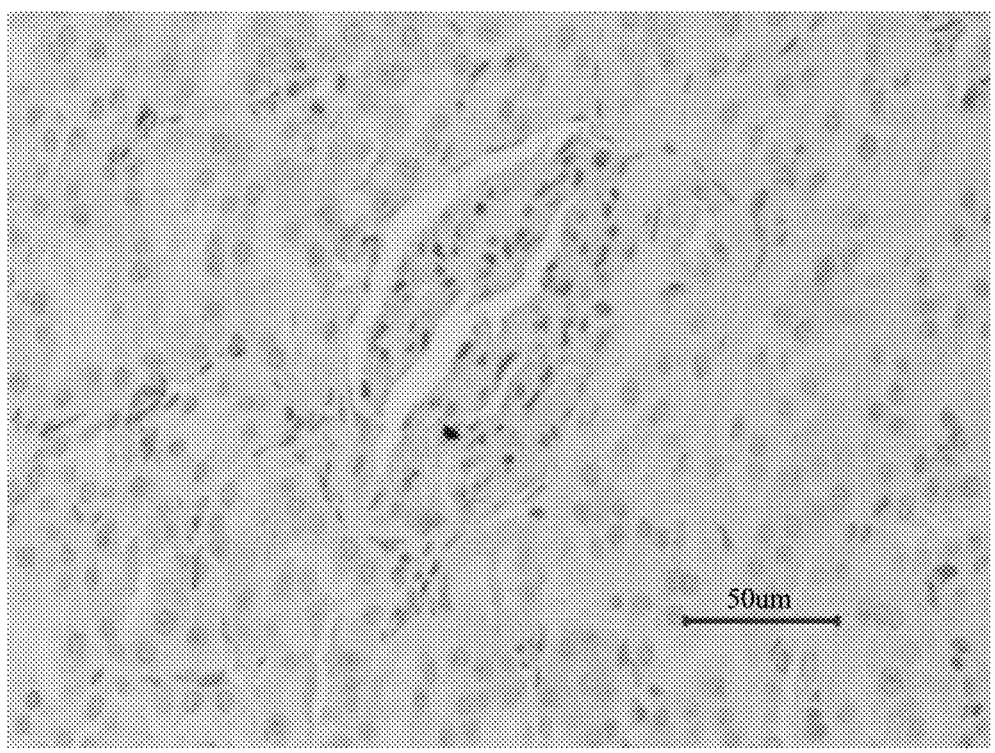
FIG. 9 is an immunohistochemical image of the No. 21 CN rat model in a high-dose group in accordance with Example 2 of the present disclosure (at a magnification of 400×)
Figure 10:
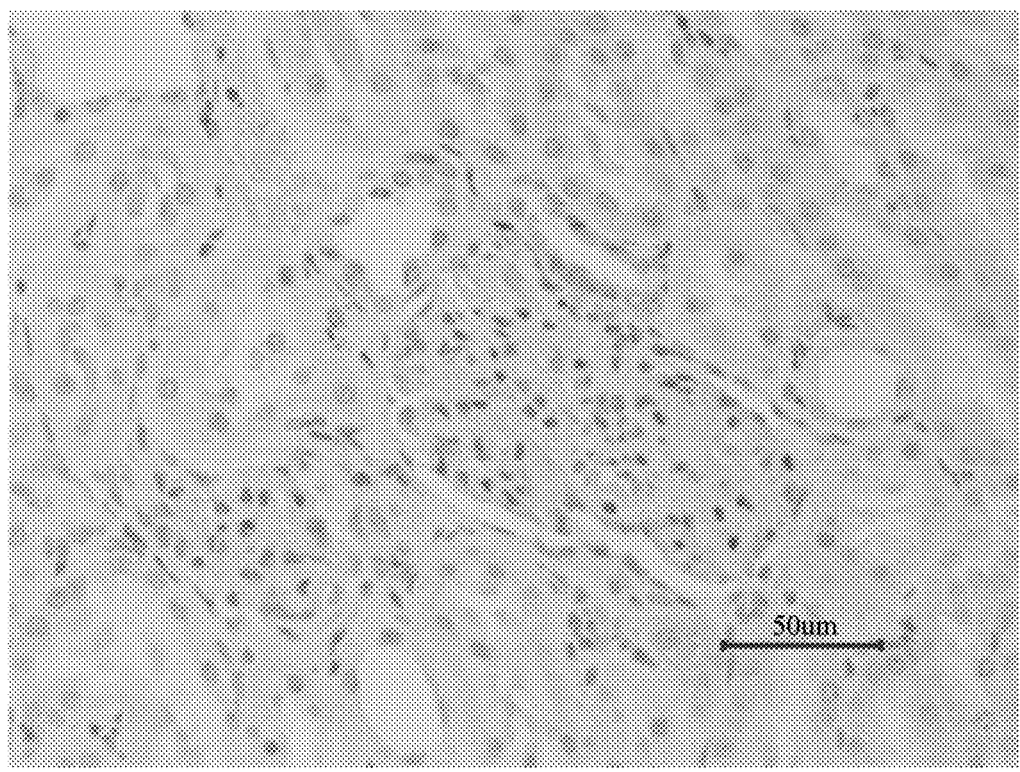
FIG. 10 is an immunohistochemical image of the No. 29 CN rat model in a high-dose group in accordance with Example 2 of the present disclosure (at a magnification of 400×)
Figure 11:
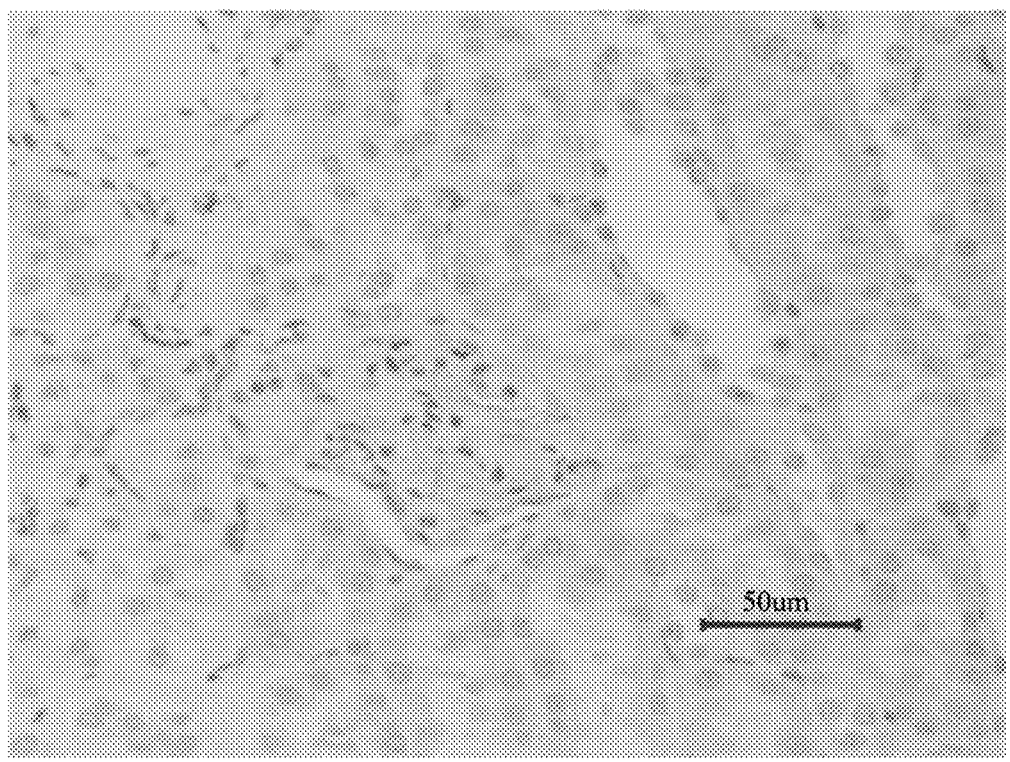
FIG. 11 is an immunohistochemical image of the No. 35 CN rat model in a medium-dose group in accordance with Example 2 of the present disclosure (at a magnification of 400×)
Figure 12:
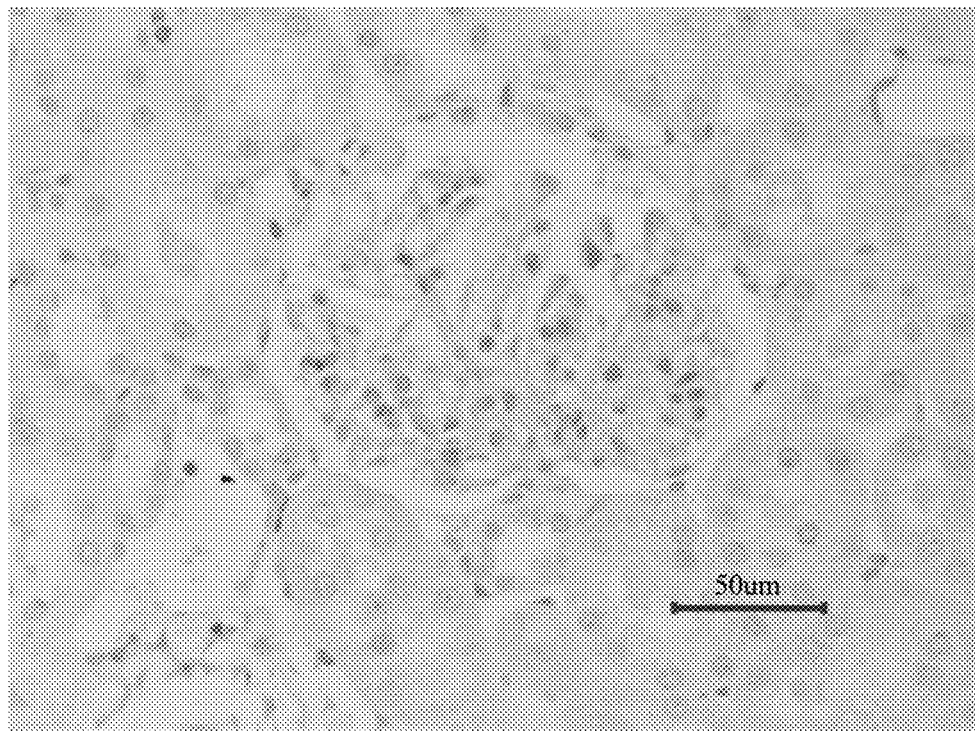
FIG. 12 is an immunohistochemical image of the No. 37 CN rat model in a medium-dose group in accordance with Example 2 of the present disclosure (at a magnification of 400×)
Figure 13:
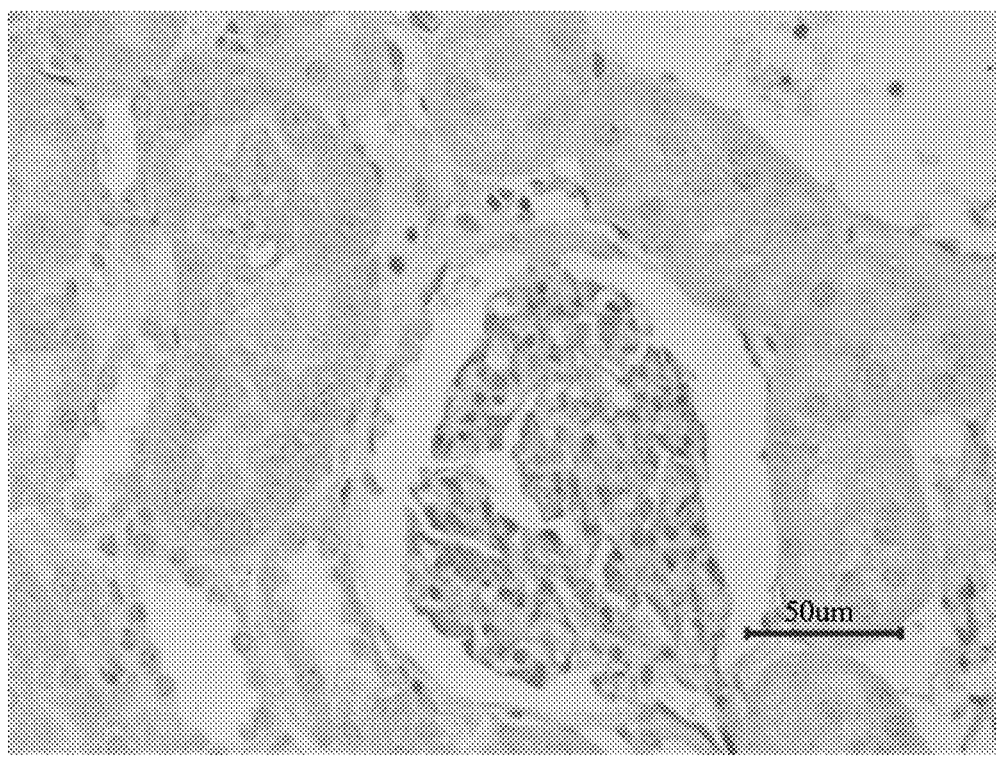
FIG. 13 is an immunohistochemical image of the No. 40 CN rat model in a low-dose group in accordance with Example 2 of the present disclosure (at a magnification of 400×)
Figure 14:
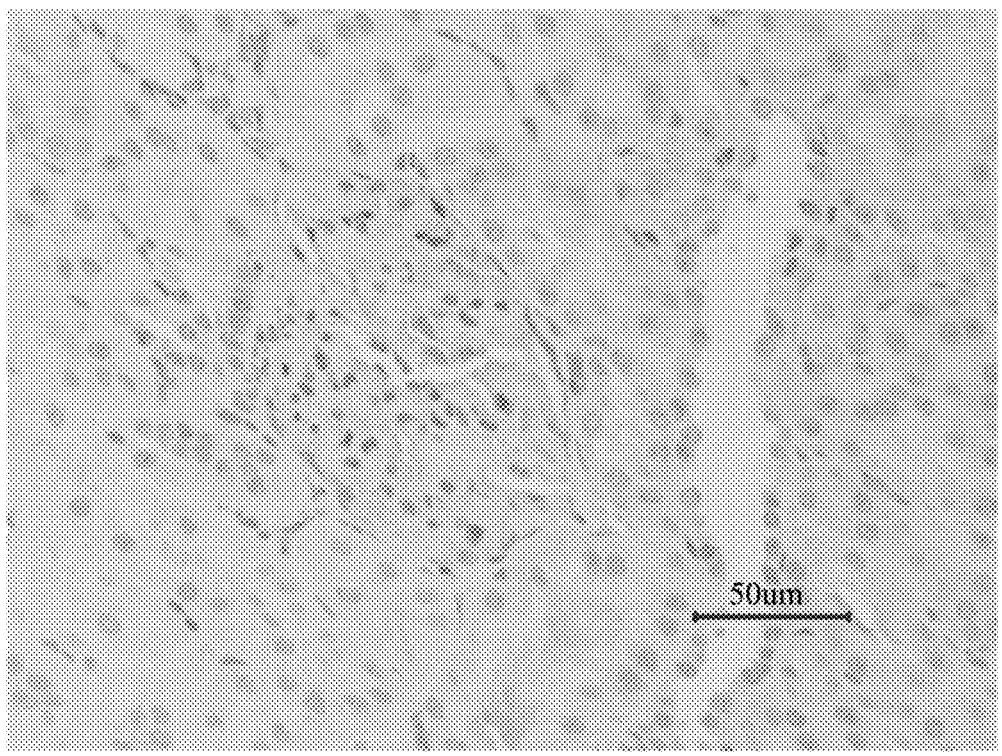
FIG. 14 is an immunohistochemical image of the No. 45 CN rat model in a low-dose group in accordance with Example 2 of the present disclosure (at a magnification of 400×)
Figure 15:
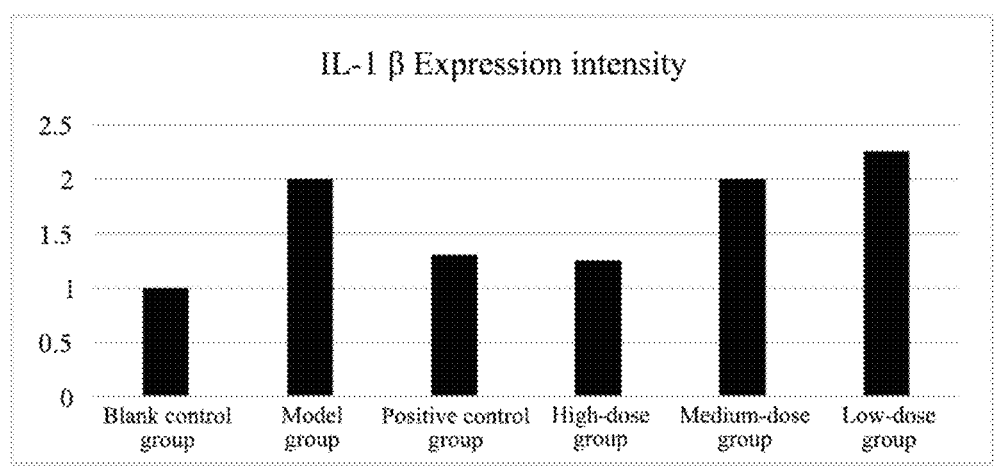
FIG. 15 schematically shows the expression results of IL-β in kidney in different groups of CN rat models in accordance with Example 2 of the present disclosure.
Figure 16:
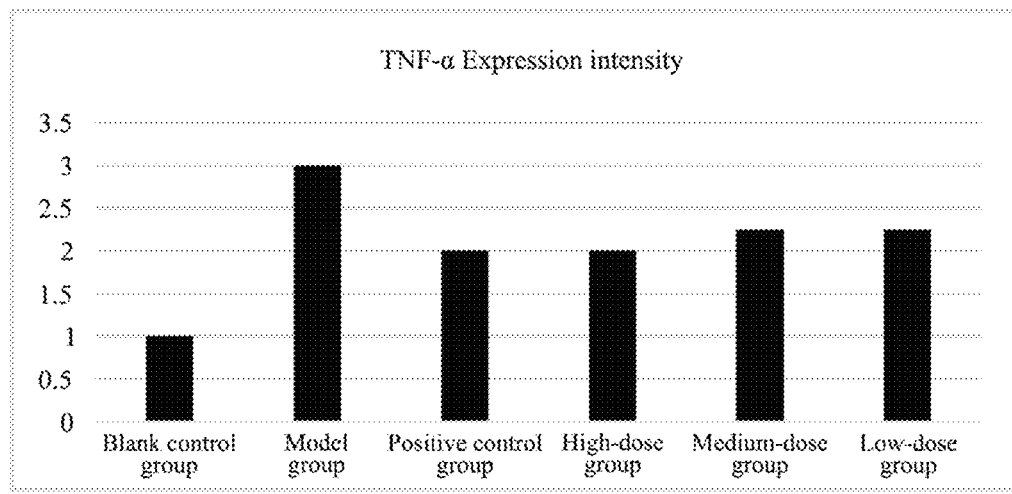
FIG. 16 schematically shows the expression results of TNF-α in kidney in different groups of CN rat models in accordance with Example 2 of the present disclosure.

As shown in FIGS. 4-16, the expression results of IL-β in kedney showed a reduced level in the blank group and an elevated level in the model group of CN. The positive control group and the high-dose group were able to reduce the expression level of IL-β in kidney, but there was no significant difference between the medium and low dose groups and the model group, and the expression level of IL-β in low-dose group was slightly higher than in the model group. There may be a relationship between the expression level of IL-β with the dose. As shown in FIGS. 4-16, the expression results of TNF-α in kidney showed that the blank group expressed at a low level, and the model group of CN showed a significantly increased expression. The positive control group and the treatment groups both showed reduced expression levels.

The embodiments described above are merely illustrative of the present disclosure, and are not intended to limit the scope of the present disclosure. Any modifications, equivalent substitutions, improvements, etc. made by those skilled in the art without departing from the spirit and principles of the present disclosure shall fall within the scope of the present disclosure defined by the appended claims.

What is claimed is:

1. A peony stamen-dodder composite for treating nephritis, wherein raw materials of the peony stamen-dodder composite comprise 10-18 parts by weight of a peony stamen and 5-12 parts by weight of a dodder; and the peony stamen-dodder composite is prepared through steps of:
    step (1) subjecting the peony stamen to desensitization, impregnation with a first saline and drying, and subjecting the dodder to impregnation with a second saline and baking; and
    step (2) crushing a treated peony stamen obtained in step (1), and crushing a treated dodder obtained in step (1); impregnating a crushed peony stamen and a crushed dodder with warm water followed by a first ultrasonic treatment and filtration to obtain a first filtrate and a filter residue; dispersing the filter residue in water followed by a second ultrasonic treatment and filtration to obtain a second filtrate; and combining the first filtrate with the second filtrate followed by vacuum concentration to obtain the peony stamen-dodder composite;
    wherein in step (1), the desensitization is performed at 120° C. for 1-3 min, or performed by microwave-assisted desensitization at a power of 3,000-5,000 W and a temperature of 65-80° C. for 1-3 min; a thickness of the peony stamen is 3-6 mm; the drying is performed at 55-65° C. for 4.5-5.5 h; the baking is performed at 75-85° C. for 7.5-8.5 h; the first saline and the second saline both have a concentration of 1.2-1.8 wt. %; a weight of the first saline is 1-2 times a weight of the peony stamen; a weight of the second saline is 0.25-2 times the weight of the peony stamen; and the impregnation of the peony stamen is performed for 8-15 min, and the impregnation of the dodder is performed for 15-25 min;
    in step (2), a weight of the warm water is 19-21 times a total weight of the peony stamen and the dodder, a temperature of the warm water is 65-75° C., and the crushed peony stamen and the crushed dodder are impregnated in the warm water for 1.5-2.5 h;
    in step (2), the first ultrasonic treatment is carried out for 25-35 min, and the second ultrasonic treatment is carried out for 55-65 min; a weight of the water for dispersing the filter residue is 14-16 times a total weight of the peony stamen and the dodder; and in step (2), a temperature of the vacuum concentration does not exceed 70° C., and the vacuum concentration is performed such that a weight of a concentrated product is 7.9-8.1 times the total weight of the peony stamen and the dodder.

2. The peony stamen-dodder composite of claim 1, wherein the raw materials of the peony stamen-dodder composite comprise 15 parts by weight of the peony stamen and 8 parts by weight of the dodder.

3. The peony stamen-dodder composite of claim 1, wherein the peony stamen is a stamen of *Paeonia ostia*, a stamen of *Paeonia rockii*, or a combination thereof.

4. A drug for treating nephritis, comprising:
a therapeutically effective amount of the peony stamen-dodder composite of claim 1; and
a pharmaceutically acceptable adjuvant.

5. A method of treating nephritis in a subject in need thereof, comprising:
administering a therapeutically effective amount of the peony stamen-dodder composite of claim 1 to the subject.

\* \* \* \* \*